(12) United States Patent
Itoh et al.

(10) Patent No.: US 8,313,195 B2
(45) Date of Patent: Nov. 20, 2012

(54) FUNDUS CAMERA

(75) Inventors: Hiroshi Itoh, Yokohama (JP); Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/704,415

(22) Filed: Feb. 11, 2010

(65) Prior Publication Data
US 2010/0208202 A1    Aug. 19, 2010

(30) Foreign Application Priority Data

Feb. 16, 2009  (JP) .................. 2009-032766

(51) Int. Cl.
 *A61B 3/14*  (2006.01)
 *A61B 3/00*  (2006.01)
 *A61B 3/10*  (2006.01)
(52) U.S. Cl. ......... 351/206; 351/200; 351/210; 351/221
(58) Field of Classification Search .................. 351/200, 351/205–206, 210, 221, 246
See application file for complete search history.

(56) References Cited

U.S. PATENT DOCUMENTS

| | | | | |
|---|---|---|---|---|
| 2002/0044435 A1* | 4/2002 | Pohlert et al. | ................... | 362/13 |
| 2002/0149746 A1* | 10/2002 | Eikelboom et al. | ........... | 351/221 |
| 2003/0016333 A1* | 1/2003 | Ono | .............. | 351/221 |
| 2003/0218688 A1* | 11/2003 | Shaw et al. | ................... | 348/370 |
| 2007/0291225 A1* | 12/2007 | Suzuki | ......................... | 351/206 |
| 2008/0212027 A1* | 9/2008 | Shimizu | ...................... | 351/206 |

FOREIGN PATENT DOCUMENTS

| | | |
|---|---|---|
| JP | 2006-174984 A | 7/2006 |
| JP | 2007-29726 A | 2/2007 |

* cited by examiner

*Primary Examiner* — Dawayne A Pinkney
(74) *Attorney, Agent, or Firm* — Carter, DeLuca, Farrell & Schmidt LLP

(57) ABSTRACT

A fundus camera includes an illumination unit configured to illuminate a fundus of a subject's eye with a visible light from a visible light source, an imaging unit which has sensitivity in a visible wavelength range and is configured to receive a reflected light from the fundus to capture a fundus image, and a light amount balance changing unit configured to independently change at least a part of a light amount emitted from LED elements wherein the visible light source includes a plurality of the LED elements discretely arranged into a ring shape.

15 Claims, 5 Drawing Sheets

FUNDUS CAMERA

BACKGROUND OF THE INVENTION

1. Field of the Invention

The present invention relates to a fundus camera that performs fundus photographing by using a plurality of light-emitting diode (LED) elements as photographing light sources.

2. Description of the Related Art

In a conventional non-mydriatic fundus camera used for a group medical examination or the like, in order to prevent miosis of a subject, a visible light cut filter is inserted before a halogen light source and only an infrared component of the halogen light source is used as observation light to illuminate the subject. Further, visible light emitted from a xenon light source is used for photographing.

With respect to light with which a fundus is illuminated, it is necessary to separate fundus illumination light and photographing light from the fundus, in order to prevent light reflected on a cornea or a crystalline lens of the subject's eye from entering into a photographic diaphragm. Thus, an illumination optical system includes a diaphragm having a ring-shaped aperture disposed in a position roughly optically conjugate with the cornea or the crystalline lens. Similarly, in positions roughly optically conjugate with a pupil, a photographic optical system includes a diaphragm having a circular aperture, and the illumination optical system includes a pupil stop having a ring-shaped aperture.

Conventionally, photographing is performed by using light emitted from a xenon tube. Recently, however, for the purpose of miniaturizing an electrical device unit, saving energy, reducing costs, and preventing heat generation of a light source unit, it has been discussed to use light sources other than the halogen light source. An LED element of high luminance that emits a white light is one of major candidates of the light source, and has been discussed as a photographing light source used in the fundus camera.

As an example, Japanese Patent Application Laid-Open No. 2007-29726 discusses a technique for using LED elements in fundus illumination. According to the technique discussed in Japanese Patent Application Laid-Open No. 2007-29726, a plurality of LED elements are arranged into a ring shape to form a ring light source, and a diameter of the ring light is variable. The diameter of the ring light is made variable in order to prevent illumination scattering light generated at an anterior eye of a subject's eye from mixing into a photographed image, and to optimize brightness and a contrast of the photographed image.

Japanese Patent Application Laid-Open No. 2006-174984 discusses a technique for uniformly illuminating a fundus by diffusing and reflecting lights emitted from a plurality of arrayed LED elements, and enabling use of various fundus photographing methods by using LED elements which can emit light with a plurality of luminescent colors.

Generally, in order to obtain a high quality image, in other words, a high contrast fundus image, the fundus needs to be uniformly illuminated with the illumination light. Thus, the light emitted from the LED element is not directly guided to the fundus to illuminate it, but diffused to remove directional characteristics.

However, the conventional xenon tube used as the photographing light source cannot control ring-shaped light amount distribution. On the other hand, the plurality of LED elements is discretely arranged into the ring shape to form an illumination ring. Hence, while each LED element can be controlled, the light amount distribution is not actively controlled by controlling the each LED element.

SUMMARY OF THE INVENTION

The present invention is directed to a fundus camera that can perform directional illumination for photographing fundus using a plurality of LED elements.

According to an aspect of the present invention, a fundus camera includes an illumination unit configured to illuminate a fundus of a subject's eye with a visible light from a visible light source, an imaging unit which has sensitivity in a visible wavelength range and is configured to receive a reflected light from the fundus to capture a fundus image, and a light amount balance changing unit configured to independently change at least a part of a light amount emitted from LED elements wherein the visible light source includes a plurality of the LED elements discretely arranged into a ring shape.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Various exemplary embodiments, features, and aspects of the invention will be described in detail below with reference to the drawings.

Figure 1:
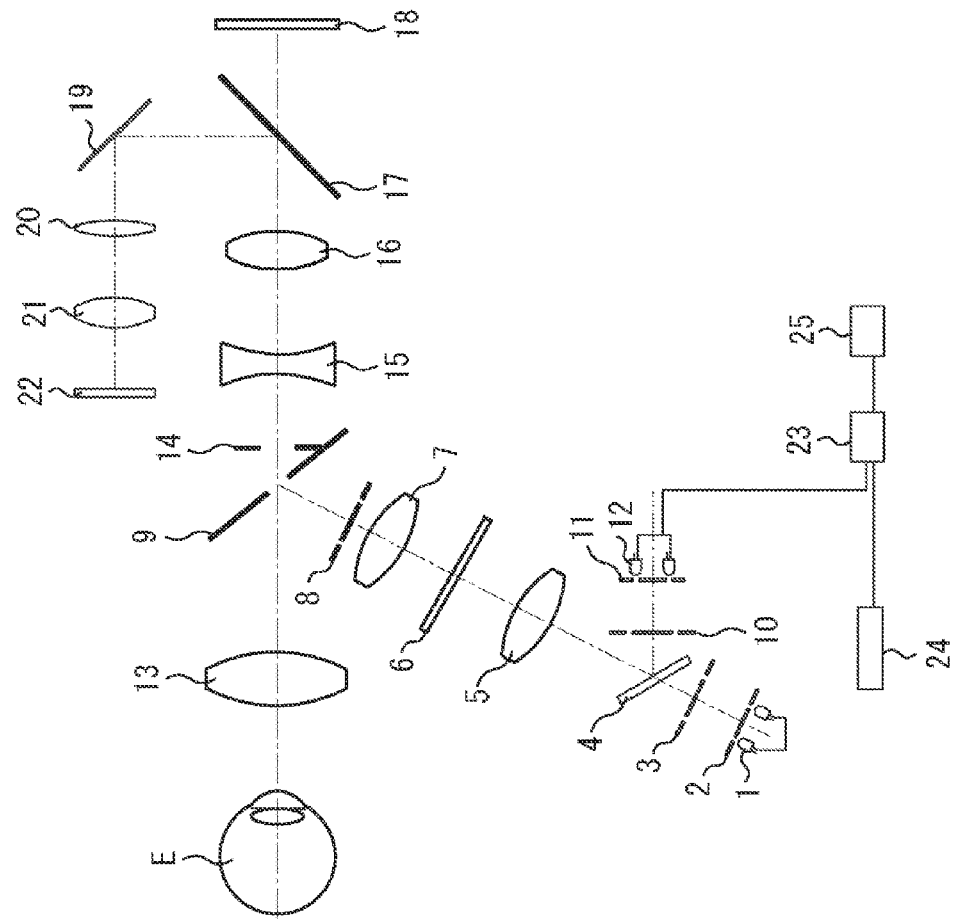
FIG. 1 illustrates a configuration of an exemplary embodiment of the present invention.

FIG. 1 illustrates a configuration of a non-mydriatic fundus camera. The non-mydriatic fundus camera includes a pupil stop 2 including a ring-shaped aperture, a crystalline lens stop 3 similarly including a ring-shaped aperture, a mirror 4, a relay lens 5, a black point plate 6, a relay lens 7, a cornea stop 8 including a ring-shaped aperture, and a perforated mirror 9, which are arranged in an emission direction of an observation illumination light source 1.

Figure 2:
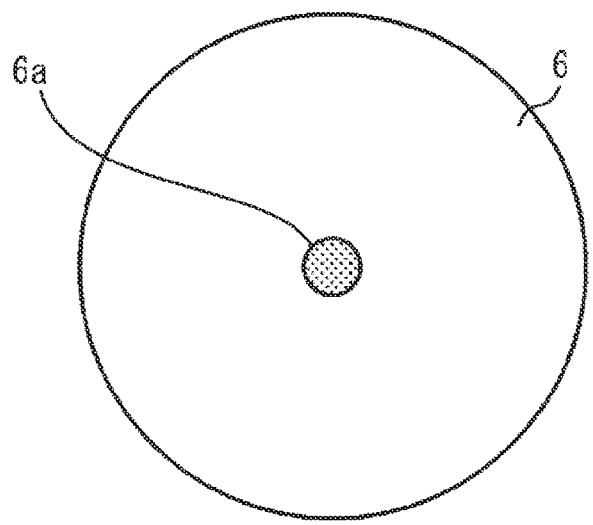
FIG. 2 is a front view of a black point plate.

The observation illumination light source 1 includes a plurality of LED elements discretely arranged into a ring shape. The black point plate 6 is configured by a glass plate which includes, in a position conjugate with a photographic diaphragm, a small shielding 6a referred to as a black point in a center as illustrated in FIG. 2.

The mirror 4 may be a flip-up mirror which has characteristics of reflecting a visible light and transmitting a near infrared light and is configured to be fixed in an optical path, or which has general total reflection characteristics, and is configured to be retracted from the optical path during observation and to be inserted thereinto during photographing.

Figure 3:
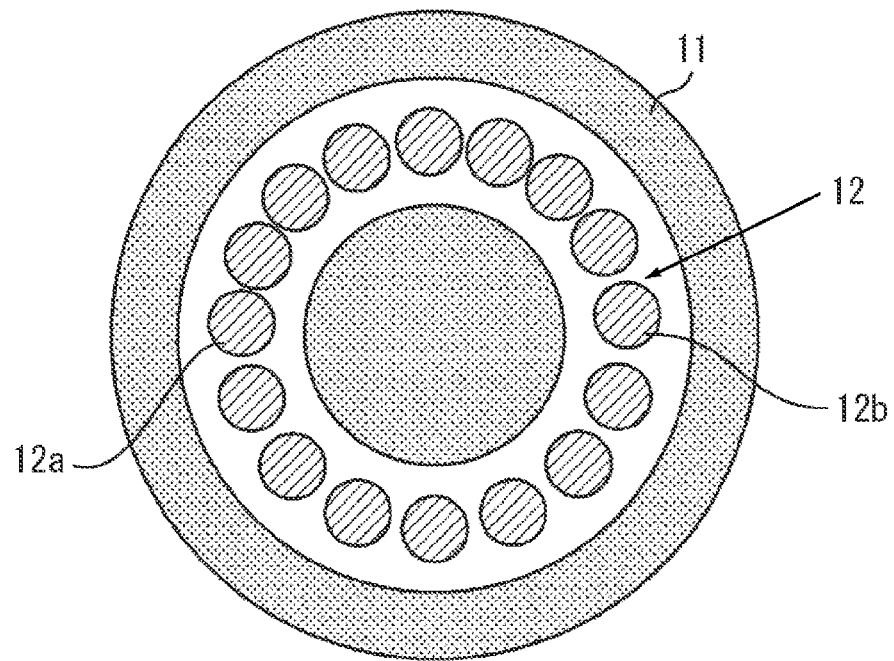
FIG. 3 illustrates arrangement of visible light LED elements.

The non-mydriatic fundus camera includes a crystalline lens stop 10 including a ring-shaped aperture, a pupil stop 11, and a photographing illumination light source 12 as a visible light source, which are arranged in an incident direction of the mirror 4. As illustrated in FIG. 3, the photographing illumination light source 12 includes a plurality of LED elements 12a and 12b discretely arranged into a ring shape along an aperture of the pupil stop 11.

An objective lens 13 is disposed between the perforated mirror 9 and a subject's eye E. An optical system from the observation illumination light source 1 and the photographing illumination light source 12 to the perforated mirror 9 and the objective lens 13 constitutes an illumination optical system.

The non-mydriatic fundus camera includes a photographic diaphragm 14, a focus lens 15, an imaging lens 16, a flip-up mirror 17 retractable from the optical path, and an imaging unit 18, which are arranged behind the perforated mirror 9. The imaging unit 18 has sensitivity in a visible wavelength range, and receives reflected light from a fundus of the subject's eye E to capture a fundus image during photographing. An optical system from the objective lens 13 to the imaging unit 18 constitutes a photographic optical system.

The non-mydriatic fundus camera includes a reflection mirror 19, a field lens 20, a relay lens 21, and an image sensor 22 which has sensitivity to a near infrared light, which are arranged in a reflection direction of the flip-up mirror 17 to constitute an observation optical system.

An output of a light amount balance changing unit 23 is connected to the photographing illumination light source 12. An output of a photographing mode selection unit 24 and an output of a left and right eye detection unit 25 configured to detect a left or right eye of the subject's eye E are connected to the light amount balance changing unit 23.

Light amounts of the LED elements 12a and 12b of the photographing illumination light source 12 can be independently changed by driving the light amount balance changing unit 23. For example, when the LED element 12a illustrated in FIG. 3 emits light, the LED element 12a takes a decentered position 12a' outside an optical axis on a pupil as illustrated in FIG. 4, and the fundus is illuminated with a light flux emitted from the LED element 12a' which is roughly in a slit shape in a longitudinal direction as indicated by a solid line.

A light flux emitted from the LED element 12b located on an opposite side of the LED element 12a takes a position 12b' on the pupil. The fundus is illuminated with the light flux emitted from the LED element 12a' which is roughly in a slit shape indicated by a dotted line. Other LED elements 12x emit illumination light according to respective angles with which an entire photographing angle of view is illuminated.

Figure 4:
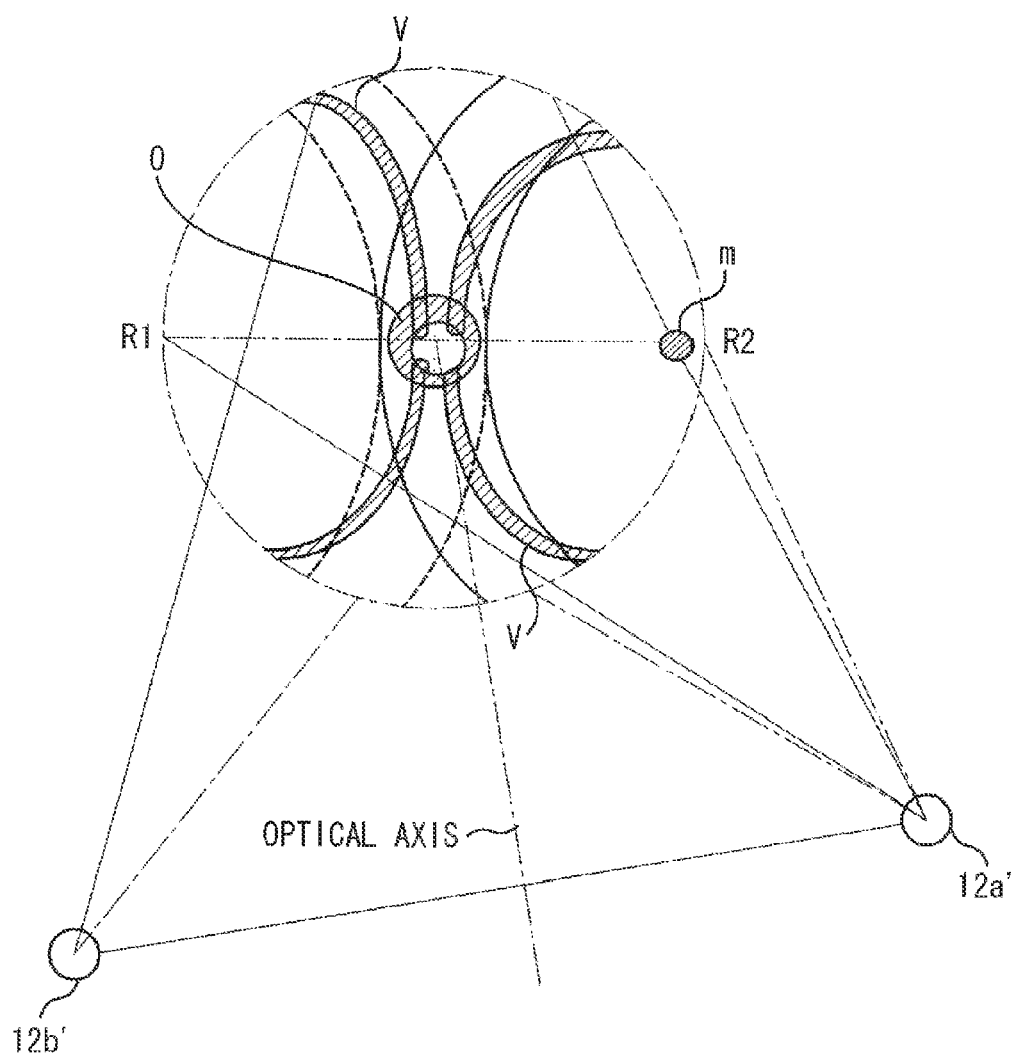
FIG. 4 illustrates a fundus portion illuminated with the visible light LED elements.
Figure 5:
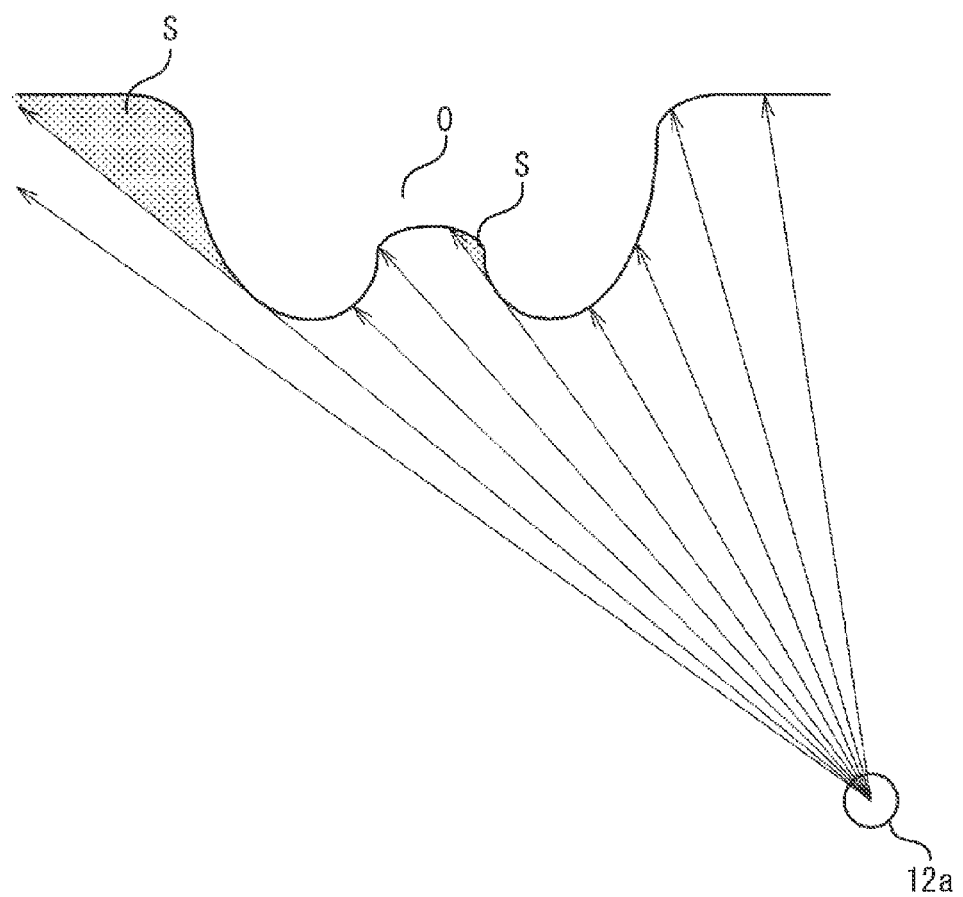
FIG. 5 illustrates a shadow portion of a fundus image.

FIG. 5 is a cross sectional view illustrating a section formed by lines connecting the position 12a' and a fundus R1-R2 of FIG. 4, especially a papillary portion O of the fundus having largest unevenness. The illumination light emitted from the position 12a' has an angle to the papillary portion O, and hence two places indicated with dots, which are referred to as shadow portions S, are shielded from the illumination light corresponding to the unevenness of the fundus.

Figure 6:
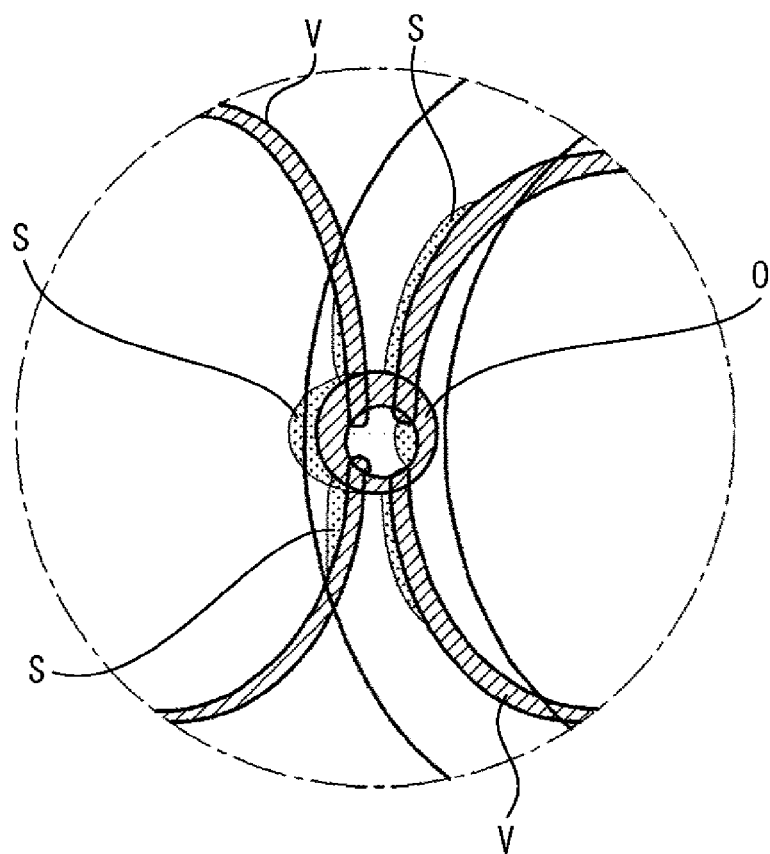
FIG. 6 illustrates a fundus image on which shadow portions are formed.

FIG. 6 illustrates a stereoscopic image which includes the shadow portions S of a fundus image which is captured based on a reflected light of the fundus. In FIG. 6, a blood vessel V on a retina is convex toward a retina surface, which is not as large as the papillary portion, and hence a shadow portion S is similarly formed.

Figure 7:
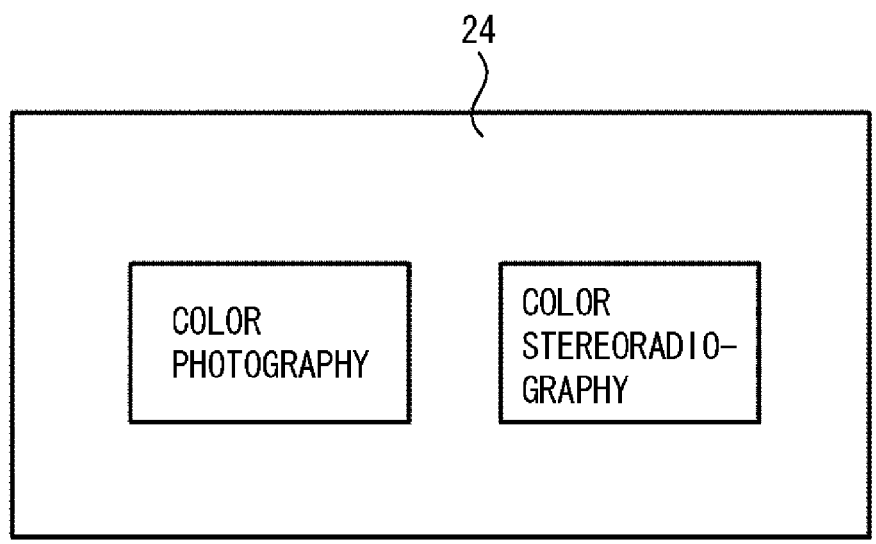
FIG. 7 is a front view of a photographing mode selection unit.

When normal color photographing of the fundus of the subject's eye E is performed, an examiner clicks a "color photography" button on the photographing mode selection unit 24 illustrated in FIG. 7. After selection of the "color photography", the light amount balance changing unit 23 drives all the LED elements 12a and 12b of the photographing illumination light source 12 to be equal in light amount irrespective of a detection result of the left and right eye detection unit 25, and performs control so as to uniformly illuminate the fundus with the light.

When the examiner presses a photographing switch (not illustrated), the light amount balance changing unit 23 is driven in synchronization with flipping up of the flip-up mirror 17, so that all the LED elements 12a and 12b of the photographing illumination light source 12 emit the light.

When the examiner clicks a "color stereoradiography" button on the photographing mode selection unit 24, the light amount balance changing unit 23 receives the detection result of the left and right eye detection unit 25, for example showing a left eye. Then the examiner presses the photographing switch, the light amount balance changing unit 23 drives the LED element 12a to form the shadow portion S on an opposite side of a macular portion m. In other words, the LED element 12a of the photographing illumination light source 12 emits the light stronger than the other LED elements 12x. As a result, the light is emitted from the position 12a' illustrated in FIG. 4, and a fundus image illustrated in FIG. 6 can be obtained.

Then, the examiner moves the fundus camera to the right eye side to capture an opposite eye to switch the left and right eyes, and clicks a "color stereoradiography" button on the photographing mode selection unit 24. Consequently, the light amount balance changing unit 23 receives the detection result (right eye) of the left and right eye detection unit 25. Thus the shadow portion S is formed on the macular portion m side when the photographing switch is pressed. In other words, when only the LED element 12b of the photographing illumination light source 12 emits the light stronger than the other LED elements 12x, as in the case of the left eye, a fundus image including the shadow portion on the macular portion m side can be captured.

In addition to these examples, only a part of the photographing illumination light source 12, for example, only the LED element 12a, emits the light during the "color stereoradiography", while the other LED elements 12x are turned off, so that the fundus image can be captured using a slit-shaped light flux.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-032766 filed Feb. 16, 2009, which is hereby incorporated by reference herein in its entirety.

What is claimed is:

1. An ophthalmologic apparatus comprising:
   an illumination unit configured to illuminate a fundus of a subject's eye with visible light from a visible light source, the visible light source including a plurality of LED elements arranged in a ring shape;
   an imaging unit which has sensitivity in a visible wavelength range and is configured to receive reflected light from the fundus of the subject's eye to capture an image of the fundus of the subject's eye; and a varying unit configured to selectively vary an amount of light emitted from a portion of the plurality of LED elements, wherein each of the plurality of LED elements is a white LED.

2. The ophthalmologic apparatus according to claim 1, wherein the varying unit causes the portion of the plurality of LED elements to strongly emit light to illuminate the fundus of the subject's eye from outside an optical axis to form a shadow portion corresponding to unevenness of the fundus of the subject's eye.

3. The ophthalmologic apparatus according to claim 1, further comprising a left and right eye detection unit configured to detect switching of the subject's eye between left and right eyes, wherein the varying unit is driven based on an output of the left and right eye detection unit.

4. The ophthalmologic apparatus according to claim 1, wherein the varying unit selectively varies the amount of light emitted from the portion of the plurality of LED elements to strongly emit light to illuminate the fundus of the subject's eye.

5. The ophthalmologic apparatus according to claim 4, wherein the varying unit is driven to change the portion of the plurality of LED elements to strongly emit the light to illuminate the fundus of the subject's eye depending on left or right eyes.

6. The ophthalmologic apparatus according to claim 1, wherein, in a color photographing mode, the varying unit selectively varies an amount of light emitted from the plurality of LED elements so that the amount of light emitted from each of the plurality of LED elements becomes substantially equal and, in a stereoradiography mode, the varying unit selectively varies an amount of light emitted from a portion of the plurality of LED elements to strongly emit light to illuminate the fundus of the subject's eye.

7. The ophthalmologic apparatus according to claim 1, wherein the varying unit selectively varies the amount of light emitted from the portion of the plurality of white LED elements to strongly emit the light to illuminate the fundus of the subject's eye.

8. The ophthalmologic apparatus according to claim 1, further comprising an observation unit configured to receive the reflected light from the fundus of the subject's eye and to form the reflected light into an image of the fundus of the subject's eye.

9. An ophthalmologic apparatus comprising:
an illumination unit configured to illuminate a fundus of a subject's eye with visible light from a visible light source, the visible light source including a plurality of LED elements; and
a varying unit configured to selectively vary an amount of light emitted from a portion of the plurality of LED elements to strongly emit light to illuminate the fundus of the subject's eye, wherein each of the plurality of LED elements is a white LED.

10. The ophthalmologic apparatus according to claim 9, wherein the plurality of LED elements is arranged in a ring shape.

11. The ophthalmologic apparatus according to claim 9, further comprising an imaging unit which has sensitivity in a visible wavelength range and is configured to receive reflected light from the fundus of the subject's eye to capture an image of the fundus of the subject's eye.

12. The ophthalmologic apparatus according to claim 9, further comprising an observation unit configured to receive reflected light from the fundus of the subject's eye and to form the reflected light into an image of the fundus of the subject's eye.

13. The ophthalmologic apparatus according to claim 9, wherein the portion of the plurality of LED elements strongly emits light to illuminate the fundus of the subject's eye from outside an optical axis to form a shadow portion corresponding to unevenness of the fundus of the subject's eye.

14. A method for ophthalmologic imaging, the method comprising:
illuminating a fundus of a subject's eye with visible light from a visible light source, the visible light source including a plurality of LED elements arranged in a ring shape;
receiving reflected light from the fundus of the subject's eye to capture an image of the fundus of the subject's eye; and
selectively varying an amount of light emitted from a portion of the plurality of LED elements, wherein each of the plurality of LED elements is a white LED.

15. The method according to claim 14, wherein selectively varying the amount of light emitted from the portion of the plurality of LED elements includes selectively varying the amount of light emitted from the portion of the plurality of LED elements to strongly emit light to illuminate the fundus of the subject's eye.

* * * * *